United States Patent
Hamamatsu et al.

(10) Patent No.: US 8,203,025 B2
(45) Date of Patent: *Jun. 19, 2012

(54) SOLID PHOSPHORIC ACID CATALYST AND METHODS OF OLEFIN DIMERIZATION REACTION WITH THE SAME

(75) Inventors: Tatsuo Hamamatsu, Yokohama (JP); Nobuhiro Kimura, Yokohama (JP); Tsutomu Takashima, Yokohama (JP); Takashi Morikita, Yokohama (JP)

(73) Assignee: Nippon Oil Corporation, Tokyo (JP)

( * ) Notice: Subject to any disclaimer, the term of this patent is extended or adjusted under 35 U.S.C. 154(b) by 652 days.

This patent is subject to a terminal disclaimer.

(21) Appl. No.: 11/920,816

(22) PCT Filed: May 25, 2006

(86) PCT No.: PCT/JP2006/310941
§ 371 (c)(1),
(2), (4) Date: Nov. 12, 2008

(87) PCT Pub. No.: WO2006/126727
PCT Pub. Date: Nov. 30, 2006

(65) Prior Publication Data
US 2009/0099400 A1   Apr. 16, 2009

(30) Foreign Application Priority Data
May 25, 2005  (JP) .................. 2005-152697

(51) Int. Cl.
*C07C 2/18* (2006.01)
(52) U.S. Cl. ........ 585/514; 502/208; 502/214; 585/502; 585/510; 585/520; 585/527; 585/529
(58) Field of Classification Search .............. 585/510, 585/514, 527, 529, 502, 520; 502/208, 214
See application file for complete search history.

(56) References Cited

U.S. PATENT DOCUMENTS

| | | | | |
|---|---|---|---|---|
| 2,186,021 A | * | 1/1940 | Holm et al. | 585/514 |
| 2,579,433 A | * | 12/1951 | Holm et al. | 585/529 |
| 2,694,686 A | * | 11/1954 | Reeves et al. | 502/214 |
| 2,909,580 A | * | 10/1959 | Layng | 585/529 |
| 3,661,801 A | | 5/1972 | Gutmann et al. | |
| 4,334,118 A | * | 6/1982 | Manning | 585/529 |
| 4,617,060 A | * | 10/1986 | Dreibelbis | 524/493 |
| 6,040,262 A | | 3/2000 | Fougret et al. | |
| 6,310,154 B1 | * | 10/2001 | Babcock et al. | 526/194 |
| 6,884,914 B2 | * | 4/2005 | Mathys et al. | 585/324 |

FOREIGN PATENT DOCUMENTS

| | | |
|---|---|---|
| JP | 47-029292 A | 11/1972 |
| JP | H07-59301 B | 6/1995 |
| JP | H08-29251 B | 3/1996 |
| JP | 2001-199907 A | 7/2001 |
| WO | WO 02/060842 | 8/2002 |

OTHER PUBLICATIONS

Clark, et al., "Supported Catalysts" in Kirk-Othmer Encyclopedia of Chemical Technology, John Wiley, 2002, posted on-line Nov. 15, 2002.*

Cavani, Fabrizio et al, "Effect of Water in the performance of the 'solid phosphoric acid' catalyst for alkylation of benzene to cumene and for oligomerization of propene," Applied Catalysis A: General, 97 (1993), pp. 177-196, Elsevier Science Publishers B.V., Amsterdam (APCAT A2489).

* cited by examiner

*Primary Examiner* — In Suk Bullock
*Assistant Examiner* — Bradley Etherton
(74) *Attorney, Agent, or Firm* — Weingarten, Schurgin, Gagnebin & Lebovici LLP

(57) ABSTRACT

The invention provides a solid phosphoric acid catalyst which has high activity and attains high dimer selectivity in olefin dimerization reactions and efficient methods of olefin dimerization. The solid phosphoric acid catalyst comprises a carrier and phosphoric acid supported thereon. When the solid phosphoric acid catalyst is heated at 250° C. for 20 minutes, heating loss of water is 50 mass % or more based on diphosphorus pentoxide ($P_2O_5$) derived from the phosphoric acid. A method of olefin dimerization comprises bringing an olefin-containing feed material containing water in an amount of 10-1000 mass ppm into contact with the catalyst to initiate the reaction.

5 Claims, No Drawings

US 8,203,025 B2

SOLID PHOSPHORIC ACID CATALYST AND METHODS OF OLEFIN DIMERIZATION REACTION WITH THE SAME

This application is a §371 national phase filing of PCT/JP2006/310941 filed May 25, 2006, and claims priority to Japanese application No. 2005-152697 filed May 25, 2005.

TECHNICAL FIELD

The present invention relates to a solid phosphoric acid catalyst comprising a phosphoric acid supported on a carrier and relates to a method of a selective olefin dimerization reaction with the same.

BACKGROUND ART

An oligomer of olefins is used for many purposes and especially a dimer of low molecular olefins (for example, propylene, n-butene, isobutene, pentenes) has importance as a base material of the high-octane number base materials for gasoline production and a chemical intermediate product. An oligomerization including a dimerization of the olefin is conducted by the use of an acid catalyst where many studies have been conducted up to the present. The acid catalysts such as sulfuric acid, hydrogen fluoride, phosphoric acid, aluminum chloride, and boron fluoride, and a solid acid such as amorphous or crystalline aluminum silicate, clay, ion exchange resin, oxide mixture, and an acid supported on carrier are given as conventional examples, and many studies on the solid phosphoric acid which can provide an inexpensive and convenient production process, have been conducted.

For example, the oligomerization method of propylene by using the solid phosphoric acid prepared under the calcination condition of 100° C. or more (Reference Patent Document 1) and the oligomerization method of propylene by using the catalyst (catalyst comprising silicone orthophosphate and silicone pyrophosphate) which is prepared by a crystallization of an amorphous mixture of the phosphoric acid and siliceous raw material under the condition of 250°-450° C. and the steam concentration 3-50 mole % (Reference Patent Document 2), have been disclosed.

Also, a condensation degree of the phosphoric acid in the solid phosphoric acid catalyst has been known to influence on the activity of the oligomerization reaction of the olefin since early times, and for example, example of the oligomerization of olefins such as $C_3$ and $C_4$ and others using supported phosphoric acid catalyst with small weight ratio of free phosphoric acid to the catalyst are disclosed. The free phosphoric acid are designated as can be eluted by immersing the catalyst in water (correspond to non-condensed or low-condensed phosphoric acid such as orthophosphoric acid and pyrophosphoric acid). Ratio of $H_2O/P_2O_5$ of such the supported phosphoric acid catalyst mentioned above corresponds to 31 mass % or less as the phosphoric acid composition. (Reference Patent Document 3, Non-Patent Document 1).

Also, according to the Reference Patent Document 3, the physical performance of the catalyst is made to deteriorate when the solid phosphoric acid catalyst is hydrated excessively, so that the hydration of the catalyst is controlled so as to make the predetermined level (corresponds to the above mentioned phosphoric acid composition) by feeding the raw material containing an adequate amount of water after conducting drying of the catalyst by hydrocarbon without containing a substantial amount of water.

However, the above mentioned methods of the oligomerization of the olefin by using conventional solid phosphoric acid catalyst are not targeted mainly to the dimerization of the olefin, and moreover, a highly polymeric product of the olefin as by-product can not be avoided by using the conventional solid phosphoric acid catalyst, so that it is difficult to obtain the olefin dimer selectively. Also, the conventional solid phosphoric acid catalyst is required to supply to the reaction in the state of small proportion of $H_2O/P_2O_5$ as the phosphoric acid composition, so that there are various inconveniences such that the water contents control is required to conduct severely so as to make water contents in the predetermined amount while preparation and storage of the catalyst (making surplus water in the catalyst so as to be small) and also drying step of the catalyst is required before the reaction.

Reference Patent Document 1: JPH08-29251B
Reference Patent Document 2: JPH07-59301B
Reference Patent Document 3: JP2001-199907A
Reference Non Patent Document 1: "Applied Catalysis A: General", 1993, 97, p. 177-196.

DISCLOSURE OF THE INVENTION

Problem to be Solved

The present invention is to provide a solid phosphoric acid catalyst having high reactivity and dimerization selectivity in the dimerization of an olefin and to provide the effective dimerization reaction method of the olefin.

Method to Solve the Problem

The first embodiment of the present invention relates to a solid phosphoric acid catalyst comprising: a phosphoric acid, including compounds forming the phosphoric acid by hydrolysis, supported on a carrier, wherein an water content of the solid phosphoric acid catalyst defined as a weight loss obtained by heating at 250° C. for 20 minutes is 50 mass % or more based on a diphosphorus pentaoxide ($P_2O_5$) derived from the phosphoric acid.

The second embodiment of the present invention relates to a method for dimerizing an olefin, wherein the dimerization reaction is started by bringing a raw material containing the olefin containing an water of 10-1000 mass ppm into contact with the solid phosphoric acid catalyst according to the first embodiment of the present invention.

The third embodiment of the present invention relates to a method for dimerizing an olefin comprising the following 3 steps sequentially:

step 1: bringing a hydrocarbon containing water of 10-1000 mass ppm and containing substantially no olefin into contact with the solid phosphoric acid catalyst according to the first embodiment of the present invention:

step 2: controlling a pressure and a temperature to the reaction initiation condition of the olefin dimerization reaction: and step 3: initiating the dimerization reaction by replacing the hydrocarbon with an olefin containing raw material containing water of 10-1000 mass ppm and bringing the olefin raw material into contact with the solid phosphoric acid catalyst.

The fourth embodiment of the present invention relates to the method for dimerizing the olefin according to the third embodiment of the present invention, wherein the temperature in the reaction initiation condition according to the step 2 is higher by 5-50° C. than the reaction temperature of the olefin dimerization reaction in a stationary state after the step 3.

Effectiveness of the Invention

The solid phosphoric acid catalyst according to the present invention is suitable especially for a dimerization reaction of an olefin where an olefin dimer is effectively produced since the preparation of catalyst is convenient, and activity and dimer selectivity are high, and a catalyst life is long. Also, by the use of the catalyst according to the present invention, the reaction can be initiated surely and stably.

BEST MODE FOR CARRYING OUT THE INVENTION

The present invention will be described in detail as follows.

As a carrier used for the solid phosphoric acid catalyst according to the present invention, materials are not limited specifically if the phosphoric acid can be supported, and preferably, the molded product of siliceous carrier such as diatomaceous earth, infusorial earth, celiate earth, Kieselguhr, kaoline, fuller's earth, artificial porous silica, and molded product of their mixture can be listed. In case that the carrier is produced by molding, the calcinations can be conducted in any temperature condition for the purpose to provide a sufficient strength, a pore volume, and a specific surface area. With respect to the molding method and the shape of the molded product, no restriction is provided specifically, and for example, various types such as granular, plate-like, and pellet-like product can be made by tablet molding, extrusion molding, spray dry, tumbling granulation, granulation in oil and the like, and the granulation size can be made to approximately 0.5-5 mm.

As the phosphoric acid, for example, an orthophosphoric acid and its condensation products (pyrophosphoric acid, polyphosphoric acid and the like) can be listed, and the chemical compounds which is hydrolyzed to the phosphoric acid (the precursor of the phosphoric acid), for example, a phosphoric acid ester of carbon number 1-8-alcohol also can be used. Also, their mixture may be used.

The proportion of the phosphoric acid to the carrier in the catalyst (The phosphoric acid is calculated as the orthophosphoric acid and the phosphoric acid other than orthophosphoric acid is calculated in terms of the orthophosphoric acid which is produced when hydrolyzed completely. Hereinafter, "the supported phosphoric acid amount") is 10-200 mass %, preferably 30-120 mass %. When the supported amount is lower than the value mentioned above, it is not preferable since the olefin dimerization reaction activity is low. Also, supporting more phosphoric acid than mentioned above is difficult.

The solid phosphoric acid catalyst according to the present invention is prepared by supporting the phosphoric acid on the carrier, and it is important that the amount of water in the catalyst obtained as the weight loss on heating the catalyst at 250° C. for 20 minutes is 50 mass % or more (0.5 mass times or more) to the diphosphorus pentaoxide ($P_2O_5$) derived from the phosphoric acid. When the amount of water obtained as weight loss on heating is below 50 mass %, it is not preferable since the reaction activity of the olefin dimerization and selectivity become low. Also, the upper limit of the amount of water obtained as the weight loss on heating differs depending on the supported phosphoric acid solution concentration and kinds of carrier, and not limited specifically, but in case of an excess amount of water, the amount of phosphoric acid supported on carrier is made to be low so that, generally, the amount of water is 1,300 mass % or less (13 mass times or less), and preferably 600 mass % or less (6 mass times), or more preferably, 400 mass % or less (4 mass times or less).

Here, the amount of $P_2O_5$ in the catalyst can be calculated by the difference between the residual amount which is obtained by subtraction of the above mentioned weight loss on heating from the catalyst mass (the total amount of the carrier and $P_2O_5$) and the carrier amount obtained by washing and drying of the catalyst. The measurement of the weight loss on heating can be conducted by the general thermogravimetric analysis and usually is carried out under the inert gas atmosphere such as $N_2$ gas and the like.

The preparation of the catalyst by supporting the phosphoric acid on the carrier can be conducted by the immersion of the carrier in the phosphoric acid solution with the subsequent removal of the surplus phosphoric acid solution. The installation used for the catalyst preparation is not specifically limited and a general batch type bath can be used and if the reactor used for the olefin dimerization reaction is applied, the catalyst preparation and the catalyst packing can be conducted simultaneously. The concentration of the phosphoric acid solution for the immersion is not limited, and the case of 92 mass % or less is preferable since the weight loss on heating can be made to the predetermined value in the immersed state, but the case of higher than 92 mass %, is not preferable since the weight loss on heating can not be attained to the predetermined level only by immersion and additional another preparation procedure of adding water is required. The concentration of the phosphoric acid solution usually used is approximately 10-80 mass % and can be varied by the targeted phosphoric acid amount on the carrier. For example, in order to make the phosphoric acid amount to 70 mass % on the carrier, the concentration of the phosphoric acid solution is, though depending on properties such as surface area and the like of the carrier, usually almost 35-45 mass %. Usually almost one hour or more of the immersion time is sufficient.

The immersion temperature is lower than 100° C. and preferably 50° C. or less. The high temperature condition as of 100° C. or more is not preferable since the weight loss on heating becomes possibly smaller than the predetermined value. Also, if the temperature is excessively low, the immersion can not be conducted because of solidification of the phosphoric acid aqueous solution, so that 0° C. or more, is preferable, and 15° C. or more is more preferable. After the immersion, by usual method such as filtration and the like, the catalyst preparation can be completed by the removal of the excess phosphoric acid solution. A special drying process to remove water is not necessary, and so far as to the extent that the weight loss on heating achieves the predetermined value, the drying process is permissible to conduct properly.

As the olefin for the olefin containing raw material, the mono-olefin having carbon numbers 3-7 is suitable, and any of straight chain, branched chain, and cyclic olefin can be used, and can be used both solely or as mixture of those olefins in accordance with the intended product. In detail, propylene, butenes (1-butene, cis-2-butene, trans-2-butene, isobutylene), n-pentenes, isopentenes, cyclopentenes, n-hexenes, isohexenes, cyclohexenes, n-heptenes, isoheptenes, and cycloheptenes can be listed. Here, the olefin dimerization is defined that 1 mole of the olefin is produced by the reaction of 2 moles of the raw material olefin (In case of the olefin mixture raw material, the mutual reaction between the different raw material olefin is included.).

According to the present invention, as the olefin, for example, butenes are suitable for use as the raw material. Among butenes dimers, isooctene is useful for the base material for high octane value gasoline. Also, high-purity di-isobutylene is useful compound for the raw material of functional chemicals as octylphenol, iso-nonionic acid and the like. In case of producing butenes dimer, one kind of butenes can be used independently, and the mixture of several types of butenes in optional proportion can be used. The composition of butenes is preferable to be adjusted depending on the application and required properties (such as octane value index and the like) of the dimers. Also, so far as to the extent that those required properties of the butene dimers are satisfied, those butenes can contain other olefin, for example, propylene, straight chain-, branched chain-, cyclic type-pentenes, hexenes, heptenes and the like.

The supply source of the olefin containing raw material is not limited specifically, for example, the olefin fraction manufactured by FCC process, the olefin fraction obtained by removing dien-component by extraction or selective hydrogenation from fraction which is manufactured by naphtha-cracker process, coker-offgas fraction, dehydrogenation reaction product and the like can be listed and their mixtures in an optional proportion also can be used.

Moreover, content of the specific fraction in those raw material can be adjusted by increasing or decreasing by using usually known method such as distillation method and the like. For example, isobutylene-isobutane fraction which contains high concentration of isobutylene can be used. Those fraction containing high concentration of isobutylene can be obtained by removing normal butenes and normal butane by distillation (or reactive distillation) of FCC—$C_4$ fraction or raffinate from butadiene extraction process of $C_4$ fraction from naphtha cracker.

In case that these fractions are used for the butenes dimerization reaction, a small amount of impurity such as butadiene and the like can be included to the extent of providing negligible effect on the reaction.

Also, for the purpose to remove reaction heat, the olefin containing raw material containing solvent can be used. Any solvent can be used if the solvent is a liquid phase while dimerization reaction condition and is essentially inactive to the solid phosphoric acid catalyst. For example, hydrocarbons such as n-paraffin, iso-paraffin, naphthenes, and aromatics and the like can be used. The saturated hydrocarbon such as butanes or like of the above mentioned raffinate or $C_4$ fraction also works as the solvent. As the amount of solvent, the ratio of olefin to total amount of olefin containing raw material which contains olefin and solvent is to be 1-70 mass %, preferably 10-65 mass %, and more preferably 15-60 mass %. The productivity falls if the solvent is excessive in amount and the heat removal effect falls if the solvent is too small in amount.

According to the present invention, the olefin containing raw material is preferable to be brought into contact with the catalyst in the liquid phase. The gas phase is not preferable since the olefin dimerization reaction activity and dimerization selectivity possibly tend to fall and the catalyst life possibly tends to be short by the occurrence of coking.

The reactor and reaction types used for the olefin dimerization reaction are not restricted specifically, and batch type, semi-batch type, continuous flow type reactions by vessel type reactor, and continuous flow type reaction by fixed bed, fluidized bed, and moving bed flow reactor, can be applied. The reaction temperature is 0-300° C., preferably 20-200° C. The temperature of less than 0° C. is not preferable since the sufficient reaction rate can not be obtained and the temperature of more than 300° C. is not preferable since side reactions increase. The reaction pressure is preferable at normal pressure to 20 MPa. The low pressure is not preferable since the reaction system may not possibly maintain the liquid phase and the high pressure is not preferable since the installation cost increases. WHSV (ratio of feed material mass to the carrier mass in one hour) is 0.1-300 hr-1, preferably 1-150 hr-1. WHSV is not preferable to be small since the production efficiency is insufficient and is not preferable to be large since the reaction does not make progress.

According to the present invention, the olefin containing raw material may be brought into contact with the solid phosphoric acid catalyst directly, but before the olefin containing raw material is brought into contact, a hydrocarbon with essentially containing no olefin (hereinafter non-olefin hydrocarbon) are preferable to be brought into contact.

Initially, a catalyst layer is filled with the non-olefin hydrocarbon and is subjected to replace by feeding of the olefin containing raw material gradually so that the radical temperature increase by the reaction heat of olefin dimerization can be inhibited. Also, by bringing into contact with the non-olefin hydrocarbon, the surplus (non-supported) phosphoric acid solution which could not be removed by filtration during the catalyst preparation can be removed. All kinds of the non-olefin hydrocarbon can be applied if essentially inactive while contacting with solid phosphoric acid catalyst, and preferable where the liquid state is made to maintain at temperature and pressure of olefin dimerization reaction initiating condition shown in the followings. For example, the hydrocarbon such as n-paraffin, iso-paraffin, naphthenes, and aromatics can be applied.

After the solid phosphoric acid catalyst is brought into contact with the non-olefin hydrocarbon, the time duration to start the olefin containing raw material feeding to the catalyst layer (hereinafter setting time), is generally 1 hour-1,000 hours, and preferably 5 hours-240 hours, wherein the temperature and pressure are made to control to the olefin dimerization reaction initiating condition. The reaction initiating condition is set so as to be able to obtain targeted activity and selectivity in the condition range of the above mentioned reaction temperature and pressure. In case that the setting time is shorter than mentioned above, to stabilize to the pre-determined condition is difficult and in case that the setting time is longer than mentioned above, it is not preferable because of deteriorating the production efficiency. In case that the temperature of the reaction initiation condition is made to be higher than the reaction condition in the stationary state brought after contacting the catalyst and the olefin containing raw material, the catalyst activity in the initial period of the olefin dimerization reaction can be made to be high and the occurrence of the side reaction can be inhibited so that the stationary state of the olefin dimerization reaction can be established immediately. The temperature of the reaction initiating condition can be set optionally depending on the target value of the initial activity and selectivity of the reaction and preferably, 5-50° C. higher than the reaction temperature in the stationary state. The higher temperature than the above is not preferable because of the occurrence of a non-targeted side reaction or the deterioration of the catalyst. In case that the temperature in the reaction initiating condition makes higher than the reaction condition in the stationary state, then subsequently, after the olefin containing raw material is fed to the catalyst layer, the reaction temperature is made so as to control to the predetermined stationary state.

According to the present invention, in order to prevent the catalyst from progressing drying (decrease of the amount of water contained in the catalyst), water is important to make to coexist with the olefin containing raw material and the non-olefin hydrocarbon brought into contact with the catalyst. The feeding method of water is not specifically restricted and the method such that the predetermined amount of water is dissolved into the olefin containing raw material by the mixing installation and subsequently feeding into the reactor, is listed. The water amount in the olefin containing raw material and non-olefin hydrocarbon is 10-1,000 mass ppm, preferably 30-500 mass ppm, and more preferably 50-300 mass ppm.

In case that the amount of water is too small, the amount of water contained in the catalyst decreases so that the activity and selectivity decrease. On the other hand, the large amount of water is not preferable since the excess amount of water (specifically exceeding amount of water to the saturated amount of water in the olefin containing raw material) makes to elute the phosphoric acid in the catalyst so that the activity decreases.

The solid phosphoric acid catalyst according to present invention, is characterized in that the selectivity of dimer in the olefin dimerization reaction is high and the side production of the oligomer of trimer or above by the reaction of dimer and the raw material olefin, can be occurred in extremely low level. Accordingly, by conducting local recycling in which a part of effluent from the reactor exit is made to recycle and to combine to the raw material feed line, the reaction heat is removed more effectively without severely damaging the dimer selectivity. The mass proportion of the recycling amount to the raw material feed amount (R/F) can be taken optionally and, for example, in case that 90% degree of conversion of the olefin dimerization reaction is targeted by using the raw material containing 40 mass % olefin, R/F is 0-50, and preferably 1-10.

EXAMPLE 1

20.0 g of 0.8-1.7 mmφ synthetic silica granular product (CARiACT Q-50 manufactured by FUJI SILISIA CHEMICAL LTD.) is immersed into 100 ml of 42 mass % phosphoric acid solution in 200 ml size beaker. After one hour of immersion, the solution is removed on the mesh filter and thereby solid phosphoric acid catalyst A is prepared. When 28 mg of the obtained catalyst is conducted to analyze by the thermogravimetric analysis under the condition of 250° C. for 20 minutes, the weight loss on heating (amount of water) is 12.6 mg (45.0 mass %), and the proportion of the total amount of carrier and $P_2O_5$ in the catalyst is 55.0 mass %. Then the mass, which is measured after the 2.00 g of catalyst is thoroughly washed and dried, is 0.71 g and the carrier amount in the catalyst is determined to be 35.5 mass %. Accordingly, the proportion of $P_2O_5$ in the catalyst is made to be 19.5 mass %, and the proportion of the weight loss on heating to $P_2O_5$ is determined as to be 230.8 mass %.

2 g of the solid phosphoric acid catalyst A is packed to the tube type stainless steel reactor (inner diameter 8 mm) and from the upper part of the reactor, the olefin containing raw material (isobutylene 30 mass %, n-butene 5 mass %, n-hexane 65 mass %, water 250 mass ppm) is fed at 21.3 g/h (WHSV=30 h−1), and a part of the effluent liquid discharged from the lower part of the reactor is made to flow together in feed as recycling (recycling ratio R/F=4). The dimerization reaction is conducted for 30 days continuously while the pressure is made as 1.0 MPa, and the temperature of the catalyst layer is made as 80° C. The reaction results are shown in Table 1.

EXAMPLE 2

2 g of the solid phosphoric acid catalyst A is packed to the tube type stainless steel reactor (inner diameter 8 mm) and from upper part of the reactor, n-hexane containing 50 ppm of water is fed at 21.3 g/h (WHSV=30 h−1), and while a part of the effluent liquid discharged from the lower part of the reactor is made to flow together in feed as recycling (recycling ratio R/F=4), the pressure and temperature are controlled to the reaction initiation condition (1.0 MPa, 80° C.). Since the pressure and temperature became stable at the reaction initiating condition in approximately one hour after feed initiation, the feeding is changed over by the olefin containing raw material (isobutylene 30 mass %, n-butene 5 mass %, n-hexane 65 mass %, water 250 mass ppm), and the dimerization reaction is conducted for 30 days continuously. The reaction results are shown in Table 1.

EXAMPLE 3

1.5 g of 0.8-1.7 mmφ synthetic silica granular product (CARiACT Q-50 manufactured by FUJI SILISIA CHEMICAL LTD.) is packed to the tube type stainless steel reactor (inner diameter 8 mm). From the lower part of the reactor, 42 mass % phosphoric acid solution is introduced as much amount as all the silica being immersed, and from the lower part of the reactor, the phosphoric acid solution is removed after one hour so that the solid phosphoric acid catalyst B is prepared. From the reactor, 2.0 g of the solid phosphoric acid catalyst B are discharged and as a result of analysis as same in EXAMPLE 1, the weight loss on heating (water) is 44.2 mass %, and the carrier and $P_2O_5$ in the catalyst are resulted in 36.6 mass % and 19.2 mass %, respectively, and the proportion of weight loss on heating to $P_2O_5$ is resulted in 230.2 mass %.

By using the solid phosphoric acid catalyst B left in the reactor, from the upper part of the reactor, n-hexane containing 50 ppm of water is fed at 23 g/h (WHSV=30 h−1), and while a part of the effluent liquid discharged from the lower part of reactor is made to flow together as recycling in feed (recycling ratio R/F=4), the pressure and temperature are controlled to the reaction initiation condition (1.0 MPa, 100° C.). Since the pressure and the temperature became stable at the reaction initiating condition in approximately one hour after feed initiation, the feeding is changed over to the olefin containing raw material (isobutylene 30 mass %, n-butene 5 mass %, n-hexane 65 mass %, water 250 mass %), and after 24 hours (one day) the temperature of the catalyst layer is changed to 80° C. and subsequently the dimerization reaction is conducted for 29 days continuously. The reaction results are shown in Table 1.

EXAMPLE 4

The catalyst preparation is conducted as same in EXAMPLE 1. However, the catalyst drying is conducted in the room of temperature 25° C. and the humidity 50% by conducting the analysis as same in EXAMPLE 1 and the solid phosphoric acid catalyst C is obtained in which the ratio of weight loss on heating to $P_2O_5$ is determined to be 51.0 mass %. The weight loss on heating (water) is 15.2 mass %, the carrier in the catalyst is 55.0 mass %, and $P_2O_5$ is 29.8 mass %.

The dimerization reaction is conducted as same in EXAMPLE 2 except using the solid phosphoric acid catalyst C. The reaction results are shown in Table 1.

EXAMPLE 5

The dimerization reaction is conducted as same in EXAMPLE 2 except that the olefin containing raw material composition is made as isobutylene 8 mass %, n-butene 27 mass %, n-hexane 65 mass %, water 250 mass ppm, and the pressure is made as 2.0 MPa, and the temperature of catalyst layer is made as 145° C. The reaction results are shown in Table 1.

EXAMPLE 6

The dimerization reaction is conducted as same in EXAMPLE 2 except that the olefin containing raw material composition is made as isopentene 20 mass %, n-pentene 20 mass %, cyclopentene 10 mass %, n-pentane 50 mass %, water 250 mass ppm, and the pressure is made as 2.0 MPa, and the temperature of catalyst layer is made as 145° C. The reaction results are shown in Table 1.

EXAMPLE 7

The dimerization reaction is conducted as same in EXAMPLE 2 except that the olefin containing raw material composition is made as isobutylene 20 mass %, n-butene 3 mass %, isopentene 7 mass %, n-pentene 10 mass %, n-hexane 60 mass %, water 250 mass ppm, and pressure is made as 1.5 MPa and the temperature of catalyst layer is made as 120° C. The reaction results are shown in Table 1.

COMPARATIVE EXAMPLE 1

The catalyst preparation is conducted as same in EXAMPLE 4, and the solid phosphoric acid catalyst D is obtained as the ratio of the weight loss on heating to $P_2O_5$ is made to be 31.5 mass %. The weight loss on heating (amount of water) at this time is 10.1 mass %, the carrier in the catalyst is 57.8 mass %, and $P_2O_5$ is 32.1 mass %.

The dimerization reaction is conducted in the same way as in EXAMPLE 2 except that the solid phosphoric acid catalyst D is used. The reaction results are shown in Table 2.

COMPARATIVE 2

The dimerization reaction is conducted as same in EXAMPLE 2 except that the olefin containing raw material (isobutylene 30 mass %, n-butene 5 mass %, n-hexane 65 mass %) of containing essentially no water is used. The reaction results are shown in Table 2.

COMPARATIVE 3

The dimerization reaction is conducted as same in EXAMPLE 2 except that the olefin containing raw material is made to isobutylene 30 mass %, n-butene 5 mass %, n-hexane 65 mass %, water 1,500 mass ppm. The reaction results are shown in Table 2.

TABLE 2

Catalyst and Reaction Result

|  |  |  | COMPARATIVE EXAMPLES | | |
|---|---|---|---|---|---|
|  |  |  | 1 | 2 | 3 |
| Catalyst weight loss on heating/$P_2O_5$ (mass %) |  |  | 31.5 | 230.8 | 230.8 |
| Water amount in olefin containing raw material (mass ppm) |  |  | 250 | 0 | 1500 |
| Reaction result | After 5 hours | Conversion of olefin % | 54 | 64 | 40 |
|  | ※1 | Dimerization selectivity % | 82 | 93 | 94 |
|  |  | Dimer yield % | 44 | 60 | 38 |
|  | After 30 days | Conversion of olefin % | 42 | 58 | 15 |
|  | ※1 | Dimerization selectivity % | 69 | 81 | 90 |
|  |  | Dimer yield % | 29 | 47 | 14 |

※1) Initiation time of feeding of olefin containing raw material is made to be starting point.

INDUSTRIAL APPLICABILITY

The solid phosphoric acid catalyst according to the present invention can be naturally applied to the industrial application of the olefin dimerization reaction, and moreover, the solid phosphoric acid catalyst according to the present invention can be used for the various reactions of using the acid catalyst such as the olefin hydration reaction and the alkylation reaction of aromatic compound and the like.

What is claimed is:

1. A solid phosphoric acid catalyst for olefin dimerization comprising: a phosphoric acid, or a compound forming the phosphoric acid by hydrolysis, supported on a porous carrier, wherein a water content of the solid phosphoric acid catalyst, defined as a weight loss obtained by heating at 250° C. for 20 minutes, is 50 mass % or more based on a diphosphorus pentoxide ($P_2O_5$) derived from the phosphoric acid.

2. A method for dimerizing an olefin, the method comprising starting the dimerization reaction by bringing a raw material containing the olefin into contact with the solid phospho-

TABLE 1

Catalyst and Reaction Result

|  |  |  | EXAMPLES | | | | | | |
|---|---|---|---|---|---|---|---|---|---|
|  |  |  | 1 | 2 | 3 | 4 | 5 | 6 | 7 |
| Catalyst weight loss on heating/$P_2O_5$ (mass %) |  |  | 230.8 | 230.8 | 230.2 | 51.0 | 230.8 | 230.8 | 230.8 |
| Water amount in olefin containing raw material (mass ppm) |  |  | 250 | 250 | 250 | 250 | 250 | 250 | 250 |
| Reaction result | After 5 hours | Conversion of olefin % | 61 | 63 | 88 | 81 | 38 | 41 | 59 |
|  | ※1 | Dimerization selectivity % | 92 | 92 | 75 | 85 | 94 | 92 | 93 |
|  |  | Dimer yield % | 56 | 58 | 66 | 69 | 36 | 38 | 55 |
|  | After 30 days | Conversion of olefin % | 84 | 84 | 87 | 83 | 51 | 53 | 78 |
|  | ※1 | Dimerization selectivity % | 82 | 83 | 83 | 84 | 92 | 90 | 86 |
|  |  | Dimer yield % | 69 | 70 | 72 | 70 | 47 | 47 | 67 |

※1) Initiation time of feeding of olefin containing raw material is made to be starting point.

ric acid catalyst according to claim 1, said raw material comprising water at 10-1000 mass ppm of said raw material, wherein the dimerization reaction, including the step of starting the reaction, is carried out in a liquid phase.

3. A method for dimerizing an olefin, the method comprising the following 3 steps carried out in a liquid phase sequentially:

step 1: bringing a hydrocarbon containing water at 10-1000 mass ppm of hydrocarbon and containing substantially no olefin into contact with the solid phosphoric acid catalyst according to claim 1;

step 2: establishing a reaction pressure and a reaction temperature of reaction initiation conditions for an olefin dimerization reaction; and step 3: initiating the dimerization reaction under the reaction initiation conditions by replacing the hydrocarbon with olefin-containing raw material and bringing the olefin-containing raw material into contact with the solid phosphoric acid catalyst, wherein said raw material comprises water at 10-1000 mass ppm of said raw material.

4. The method for dimerizing an olefin according to claim 3, wherein the temperature in the reaction initiation conditions according to step 2 is higher by 5-50° C. than the reaction temperature of the olefin dimerization reaction in a steady state after step 3.

5. The solid phosphoric acid catalyst of claim 1, wherein the porous carrier is a molded product of a siliceous carrier selected from the group consisting of diatomaceous earth, infusorial earth, celiate earth, kieselguhr, kaoline, fuller's earth, artificial porous silica, or a mixture thereof.

* * * * *

UNITED STATES PATENT AND TRADEMARK OFFICE
CERTIFICATE OF CORRECTION

| | | |
|---|---|---|
| PATENT NO. | : 8,203,025 B2 | Page 1 of 1 |
| APPLICATION NO. | : 11/920816 | |
| DATED | : June 19, 2012 | |
| INVENTOR(S) | : Tatsuo Hamamatsu et al. | |

It is certified that error appears in the above-identified patent and that said Letters Patent is hereby corrected as shown below:

On the Title page, Item (75) Inventors reads:

"Tatsuo Hamamatsu, Yokohama (JP);
Nobuhiro Kimura, Yokohama (JP);
Tsutomu Takashima, Yokohama (JP);
Takashi Morikita, Yokohama (JP)"

Should read,

--Tatsuo Hamamatsu, Yokohama-shi (JP);
Nobuhiro Kimura, Yokohama-shi (JP);
Tsutomu Takashima, Yokohama-shi (JP);
Takashi Morikita, Yokohama-shi (JP)--.

Signed and Sealed this
Eighteenth Day of June, 2013

Teresa Stanek Rea
*Acting Director of the United States Patent and Trademark Office*